US008460278B2

(12) United States Patent
Muller

(10) Patent No.: US 8,460,278 B2
(45) Date of Patent: Jun. 11, 2013

(54) EYE THERAPY SYSTEM

(75) Inventor: David Muller, Boston, MA (US)

(73) Assignee: Avedro, Inc., Waltham, MA (US)

(*) Notice: Subject to any disclaimer, the term of this patent is extended or adjusted under 35 U.S.C. 154(b) by 717 days.

(21) Appl. No.: 12/572,019

(22) Filed: Oct. 1, 2009

(65) Prior Publication Data
US 2010/0094280 A1 Apr. 15, 2010

Related U.S. Application Data

(60) Provisional application No. 61/101,820, filed on Oct. 1, 2008.

(51) Int. Cl.
*A61B 18/18* (2006.01)
(52) U.S. Cl.
USPC .................. 606/4; 606/41; 607/141
(58) Field of Classification Search
USPC .............. 606/4, 5, 6, 33, 41; 607/141
See application file for complete search history.

(56) References Cited

U.S. PATENT DOCUMENTS

| 3,776,230 | A | | 12/1973 | Neefe |
| 4,326,529 | A | | 4/1982 | Doss et al. |
| 4,381,007 | A | * | 4/1983 | Doss ........................ 606/27 |
| 4,490,022 | A | | 12/1984 | Reynolds |
| 4,712,543 | A | | 12/1987 | Baron |
| 4,743,725 | A | | 5/1988 | Risman |
| 4,796,623 | A | | 1/1989 | Krasner et al. |
| 4,805,616 | A | | 2/1989 | Pao |
| 4,881,543 | A | | 11/1989 | Trembly et al. |
| 4,891,043 | A | | 1/1990 | Zeimer et al. |
| 4,994,058 | A | | 2/1991 | Raven et al. |
| 5,019,074 | A | * | 5/1991 | Muller ........................ 606/5 |
| 5,080,660 | A | * | 1/1992 | Buelna ....................... 606/45 |
| 5,103,005 | A | | 4/1992 | Gyure et al. |

(Continued)

FOREIGN PATENT DOCUMENTS

| EP | 1 561 440 | 8/2005 |
| EP | 2 269 531 | 1/2011 |

(Continued)

OTHER PUBLICATIONS

Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).

(Continued)

*Primary Examiner* — Linda Dvorak
*Assistant Examiner* — Jocelyn D Ram
(74) *Attorney, Agent, or Firm* — Nixon Peabody LLP

(57) ABSTRACT

A system includes a conducting element that conducts energy from an energy source to apply therapy to an eye. The system includes a covering configured to be removably attached to the conducting element. The covering has an interface surface that is positionable at an eye. At least a portion of the interface surface includes one or more dielectric materials. Energy is deliverable to the eye through the interface surface. In one aspect, the covering provides an electrical insulator to minimize the concentration of electrical current in the area of contact with the eye. In another aspect, the covering allows the eye to be cooled during the application of energy without directly applying coolant to the eye. In another aspect, the covering includes a dielectric layer that may provide varying impedances that allow different patterns for energy delivery. In another aspect, the sheath promotes hygienic use of the conducting element.

44 Claims, 12 Drawing Sheets

U.S. PATENT DOCUMENTS

| | | | |
|---|---|---|---|
| 5,171,254 A | 12/1992 | Sher | |
| 5,281,211 A | 1/1994 | Parel et al. | |
| 5,332,802 A | 7/1994 | Kelman et al. | |
| 5,370,644 A | 12/1994 | Langberg | |
| 5,437,658 A | 8/1995 | Muller et al. | |
| 5,461,212 A | 10/1995 | Seiler et al. | |
| 5,490,849 A | 2/1996 | Smith | |
| 5,586,134 A | 12/1996 | Das et al. | |
| 5,618,284 A | 4/1997 | Sand | |
| 5,624,456 A | 4/1997 | Hellenkamp | |
| 5,634,921 A | 6/1997 | Hood et al. | |
| 5,658,278 A | 8/1997 | Imran et al. | |
| 5,695,448 A * | 12/1997 | Kimura et al. | 600/121 |
| 5,766,171 A | 6/1998 | Silvestrini | |
| 5,779,696 A | 7/1998 | Berry et al. | |
| 5,814,040 A | 9/1998 | Nelson et al. | |
| 5,830,139 A | 11/1998 | Abreu | |
| 5,873,901 A | 2/1999 | Wu et al. | |
| 5,885,275 A | 3/1999 | Muller | |
| 5,910,110 A | 6/1999 | Bastable | |
| 5,919,222 A | 7/1999 | Hjelle et al. | |
| 5,941,834 A * | 8/1999 | Skladnev et al. | 600/587 |
| 6,033,396 A | 3/2000 | Huang et al. | |
| 6,053,909 A | 4/2000 | Shadduck | |
| 6,104,959 A | 8/2000 | Spertell | |
| 6,120,434 A * | 9/2000 | Kimura et al. | 600/114 |
| 6,139,876 A | 10/2000 | Kolta | |
| 6,149,646 A | 11/2000 | West, Jr. et al. | |
| 6,161,544 A | 12/2000 | DeVore et al. | |
| 6,162,210 A | 12/2000 | Shadduck | |
| 6,293,938 B1 | 9/2001 | Muller | |
| 6,319,273 B1 | 11/2001 | Chen et al. | |
| 6,325,792 B1 | 12/2001 | Swinger et al. | |
| 6,334,074 B1 | 12/2001 | Spertell | |
| 6,342,053 B1 | 1/2002 | Berry | |
| 6,402,739 B1 | 6/2002 | Neev | |
| 6,413,255 B1 | 7/2002 | Stern | |
| 6,520,956 B1 | 2/2003 | Huang | |
| 6,617,963 B1 | 9/2003 | Watters et al. | |
| 6,749,604 B1 | 6/2004 | Eggers et al. | |
| 6,918,906 B2 * | 7/2005 | Long | 606/41 |
| 6,946,440 B1 | 9/2005 | DeWoolfson | |
| 7,044,945 B2 | 5/2006 | Sand | |
| 7,130,835 B2 | 10/2006 | Cox et al. | |
| 7,141,049 B2 | 11/2006 | Stern et al. | |
| 7,192,429 B2 | 3/2007 | Trembly | |
| 7,270,658 B2 | 9/2007 | Woloszko et al. | |
| 7,402,562 B2 | 7/2008 | DeWoolfson | |
| 7,713,268 B2 | 5/2010 | Trembly | |
| 7,875,024 B2 * | 1/2011 | Turovskiy et al. | 606/33 |
| 7,976,542 B1 * | 7/2011 | Cosman et al. | 606/41 |
| 8,202,272 B2 * | 6/2012 | Muller et al. | 606/41 |
| 2002/0002369 A1 | 1/2002 | Hood | |
| 2002/0013579 A1 | 1/2002 | Silvestrini | |
| 2002/0049437 A1 | 4/2002 | Silvestrini | |
| 2002/0077699 A1 | 6/2002 | Olivieri et al. | |
| 2002/0099363 A1 | 7/2002 | Woodward et al. | |
| 2002/0164379 A1 | 11/2002 | Nishihara et al. | |
| 2003/0018255 A1 | 1/2003 | Martin et al. | |
| 2003/0097130 A1 | 5/2003 | Muller et al. | |
| 2003/0175259 A1 | 9/2003 | Karageozian | |
| 2003/0216728 A1 | 11/2003 | Stern et al. | |
| 2004/0001821 A1 | 1/2004 | Silver et al. | |
| 2004/0111086 A1 | 6/2004 | Trembly | |
| 2004/0143250 A1 | 7/2004 | Trembly | |
| 2004/0199158 A1 | 10/2004 | Hood et al. | |
| 2004/0243160 A1 | 12/2004 | Shiuey et al. | |
| 2005/0033202 A1 | 2/2005 | Chow et al. | |
| 2005/0070977 A1 | 3/2005 | Molina | |
| 2005/0197657 A1 | 9/2005 | Goth et al. | |
| 2005/0287217 A1 | 12/2005 | Levin et al. | |
| 2006/0135957 A1 | 6/2006 | Panescu | |
| 2006/0149343 A1 | 7/2006 | Altshuler et al. | |
| 2006/0189964 A1 | 8/2006 | Anderson et al. | |
| 2006/0206110 A1 | 9/2006 | Knowlton et al. | |
| 2006/0254851 A1 | 11/2006 | Karamuk | |
| 2006/0287662 A1 | 12/2006 | Berry et al. | |
| 2007/0048340 A1 | 3/2007 | Ferren et al. | |
| 2007/0055227 A1 | 3/2007 | Khalaj et al. | |
| 2007/0074722 A1 | 4/2007 | Giroux et al. | |
| 2007/0074730 A1 * | 4/2007 | Nanduri et al. | 128/897 |
| 2007/0114946 A1 | 5/2007 | Goetze et al. | |
| 2007/0123845 A1 | 5/2007 | Lubatschowski | |
| 2007/0161976 A1 | 7/2007 | Trembly | |
| 2007/0179564 A1 | 8/2007 | Harold | |
| 2007/0203547 A1 | 8/2007 | Costello et al. | |
| 2007/0233057 A1 * | 10/2007 | Konishi | 606/33 |
| 2007/0244470 A1 | 10/2007 | Barker et al. | |
| 2007/0244496 A1 | 10/2007 | Hellenkamp | |
| 2008/0015660 A1 | 1/2008 | Herekar | |
| 2008/0027328 A1 | 1/2008 | Klopotek et al. | |
| 2009/0024117 A1 | 1/2009 | Muller | |
| 2009/0054879 A1 | 2/2009 | Berry | |
| 2009/0069798 A1 | 3/2009 | Muller et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0187173 A1 | 7/2009 | Muller | |
| 2009/0209954 A1 | 8/2009 | Muller et al. | |
| 2010/0094197 A1 | 4/2010 | Marshall et al. | |
| 2010/0179531 A1 * | 7/2010 | Nebrigic et al. | 606/33 |

FOREIGN PATENT DOCUMENTS

| | | |
|---|---|---|
| WO | WO 99/17690 | 4/1999 |
| WO | WO 00/09027 | 2/2000 |
| WO | 0074648 A2 | 12/2000 |
| WO | WO 2004/052223 | 6/2004 |
| WO | 2006128038 A2 | 11/2006 |
| WO | WO 2007/022993 | 3/2007 |
| WO | WO 2007/120457 A2 | 10/2007 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).

Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).

Andreassen TT, Simonsen AH, Oxlund H, "Biomechanical Properties of Keratoconus and Normal Corneas," *Experimental Eye Research*, vol. 31, Oct. 1980, pp. 435-441 (7 pages).

Anschutz T, "Laser Correction of Hyperopia and Presbyopia," *International Ophthalmology Clinics*, vol. 34, No. 4, Fall 1994, pp. 107-137 (33 pages).

Bailey MD, Zadnik K, "Outcomes of LASIK for Myopia With FDA-Approved Lasers," *Cornea*, vol. 26, No. 3, Apr. 2007, pp. 246-254 (9 pages).

Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).

Bower KS, Weichel ED, Kim TJ, "Overview of Refractive Surgery," *Am Fam Physician*, vol. 64, No. 7, Oct. 2001, pp. 1183-1190 (8 pages).

Braun EH, Lee J, Steinert RF, "Monovision in Lasik," *Ophthalmology*, vol. 115, No. 7, Jul. 2008, pp. 1196-1202 (7 pages).

Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).

Bryant ME, McDonnell PJ, "Constitutive Laws for Biomechanical Modeling of Refractive Surgery," Journal of Biomechanical Engineering, vol. 118, Nov. 1996, pp. 473-481 (10 pages).

Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).

Charman WN, "The Eye in Focus: Accommodation and Presbyopia," *Clinical and Experimental Optometry*, vol. 91, May 2008, pp. 207-225 (19 pages).

Corbett et al, "Effect of Collagenase Inhibitors on Coreal Haze after PRK", Exp. Eye Res., vol. 72, Issue 3, pp. 253-259, dated Jan. 29, 2001 (7 pages).

Cox CA, Krueger RR, "Monovision with Laser Vision Correction," Ophthalmology Clinics of North Amermica, vol. 19, No. 1, Mar. 2006, pp. 71-75 (7 pages).

Doss JD, Albillar JI, "A Technique for the Selective Heating of Corneal Stroma," Contact & Intraocular Lens Medical Journal, vol. 6, No. 1, Jan.- Mar. 1980, pp. 13-17 (8 pages).

Elsheikh A, Anderson K, "Comparative Study of Corneal Strip Extensometry and Inflation Tests," Journal of the Royal Society Interface, vol. 2, May 2005, pp. 177-185 (10 pages).

Evans BJW, "Monovision: a Review," Ophthalmic and Physiological Optics, vol. 27, Jan. 2007, pp. 417-439 (23 pages).

Gasset AR, Kaufman HE, "Thermokeratoplasty in the Treatment of Keratoconus," American Journal of Ophthalmology, vol. 79, Feb. 1975, pp. 226-232 (8 pages).

Gloster J, Perkins ES, "The Validity of the Imbert-Flick Law as Applied to Applanation Tonometry," Experimental Eye Research, vol. 2, Jul. 1963, pp. 274-283 (10 pages).

Gupta N, Naroo SA, "Factors Influencing Patient Choice of Refractive Surgery or Contact Lenses and Choice of Centre," Contact Lens & Anterior Eye, vol. 29, Mar. 2006, pp. 17-23 (7 pages).

Hamilton DR, Hardten DR, Lindstrom RL, "Thermal Keratoplasty," Cornea, $2^{nd}$ Edition, Chapter 167, 2005, pp. 2033-2045 (13 pages).

Hersh PS, "Optics of Conductive Keratoplasty: Implication for Presbyopia Management," Transactions of the American Ophthalmological Society, vol. 103, 2005, pp. 412-456 (45 pages).

Hjortdal JO, "Extensibility of the Normo-Hydrated Human Cornea," Acta Ophthalmologica Scandinavica, vol. 73, No. 1, Feb. 1995, pp. 12-17 (7 pages).

Hori-Komai Y, Toda I, Asano-Kato N, Tsubota K, "Reasons for Not Performing Refractive Surgery," Journal of Cataract & Refractive Surgery, vol. 28, May 2002, pp. 795-797 (3 pages).

Illueca C, Alié JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," Journal of Refractive Surgery, vol. 24, Apr. 2008, pp. 344-349 (6 pages).

Jain S, Arora I, Azar DT, "Success of Monovision in Presbyopes: Review of the Literature and Potential Applications to Refractive Surgery," Survey of Ophthalmology, vol. 40, No. 6, May-Jun. 1996, pp. 491-499 (9 pages).

Tin GJC, Lyle A, Merkley KH, "Laser in Situ Keratomileusis for Primary Hyperopia," Journal of Cataract & Refractive Surgery, vol. 31, Apr. 2005, pp. 776-784 (9 pages).

Llovet F, Galal A, Benitez-del-Castillo J-M, Ortega J, Martin C, Baviera J, "One-Year Results of Excimer Laser in Situ Keratomileusis for Hyperopia," Journal of Cataract & Refractive Surgery, vol. 35, Jul. 2009, pp. 1156-1165 (10 pages).

Louie TM, Applegate D, Kuenne CB, Choi LJ, Horowitz DP, "Use of Market Segmentation to Identify Untapped Consumer Needs in Vision Correction Surgery for Future Growth," Journal of Refractive Surgery, vol. 19, No. 5, Sep.-Oct. 2003, pp. 566-576 (12 pages).

Maxwell WA, Lane SS, Zhou F, "Performance of Presbyopia-Correcting Intraocular Lenses in Distance Optical Bench Tests," Journal of Cataract & Refractive Surgery, vol. 35, Jan. 2009, pp. 166-171 (6 pages).

McDonald MB, Durrie D, Asbell P, Maloney R, Nichamin L, "Treatment of Presbyopia With Conductive Keratoplasty: Six-Month Results of the 1-Year United States FDA Clinical Trial," Cornea, vol. 23, No. 7, Oct. 2004, pp. 661-668 (8 pages).

McDonald MB, "Conductive Keratoplasty: a Radiofrequency-Based Technique for the Correction of Hyperopia," Transactions of the American Ophthalmological Society, vol. 103, Dec. 2005, pp. 512-536 (25 pages).

Moriera MD, Garbus JJ, Fasano A, Lee M, Clapham TN, McDonnel PJ, "Multifocal Corneal Topographic Changes With Excimer Laser Photorefractive Keratectomy," Archives of Ophthalmology, vol. 110, Jul. 1992, pp. 994-999 (6 pages).

Nash IS, Greene PR, Foster CS, "Comparison of Mechanical Properties of Keratoconus and Normal Corneas," Experimental Eye Research, vol. 35, 1982, pp. 413-424 (12 pages).

Newman JM, "Analysis, Interpretation, and Prescription for the Ametropias and Heterophorias," Borish's Clinical Refraction, 1998, pp. 776-822 (49 pages).

Pandolfi A, Manganiello F, "A Model for the Human Cornea: Formulation and Numerical Analysis," Biomechanics and Modeling in Mechanobiology, vol. 5, Jan. 2006, pp. 237-246 (10 pages).

Pertaub R, Ryan TP, "Numerical Model and Analysis of an Energy-Based System Using Microwaves for Vision Correction," Proceedings of SPIE, vol. 7181, Feb. 2009, p. 718105-1 to 718105-14 (14 pages).

Petroll WM, Roy P, Chuong CT, Hall B, Cavanagh HD, Jester JV, "Measurement of Surgically Induced Corneal Deformations Using Three-Dimensional Confocal Microscopy," Cornea, vol. 15, No. 2, Mar. 1996, pp. 154-164 (12 pages).

Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," Journal of Refractive Surgery, vol. 24, May 2008, pp. 494-500 (7 pages).

Pinsky PM, Datye DV, "A Microstructurally-Based Finite Element Model of the Incised Human Cornea," Journal of Biomechanics, vol. 24, No. 10, Apr. 1991, pp. 907-922 (15 pages).

Pinsky PM, Datye DV, "Numerical Modeling of Radial, Astigmatic, and Hexagonal Keratotomy," Refractive and Corneal Surgery, vol. 8, No. 2, Mar.-Apr. 1992, pp. 164-172 (11 pages).

Pinsky PM, van der Heide D, Chernyak D, "Computational Modeling of Mechanical Anisotropy in the Cornea and Sclera," Journal of Cataract & Refractive Surgery, vol. 31, Jan. 2005, pp. 136-145 (10 pages).

Riley C, Chalmers RL, "Survey of Contact Lens-Wearing Habits and Attitudes Toward Methods of Refractive Correction: 2002 Versus 2004," Optometry and Vision Science, vol. 82, No. 6, Jun. 2005, pp. 555-561 (7 pages).

Rosenbloom A, "New Aged and Old Aged: Impact of the Baby Boomer," Journal of the American Optometry Association, vol. 74, No. 4, Apr. 2003, pp. 211-213 (5 pages).

Rutzen AR, Roberts CW, Driller J, Gomez D, Lucas BC, Lizzi FL, Coleman DJ., "Production of Corneal Lesions Using High-Intensity Focused Ultrasound," Cornea, vol. 9, No. 4, Oct. 1990, pp. 324-330 (8 pages).

Ryan TP, Pertaub R, Meyers SR, Dresher RP, Scharf R., "Experimental Results of a New System Using Microwaves for Vision Correction," Proceedings of SPIE, vol. 7181, Feb. 2009, pp. 718106.1 to 718106.17 (17 pages).

Seiler T, Matallana M, Bende T, "Laser Thermokeratoplasty by Means of a Pulsed Holmium: YAG Laser for Hyperopic Correction," Refractive and Corneal Surgery, vol. 6, No. 5, Sep.-Oct. 1990, pp. 335-339 (6 pages).

Seiler T, Matallana M, Sendler S, Bende T, "Does Bowman's Layer Determine the Biomechanical Properties of the Cornea?" Refractive and Corneal Surgery, vol. 8, No. 2, Mar.-Apr. 1992, pp. 139-142 (6 pages).

Shin TJ, Vito RP, Johnson LW, McCarey BE, "The Distribution of Strain in the Human Cornea," Journal of Biomechanics, vol. 30, No. 5, May 1997, pp. 497-503 (7 pages).

Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," Ophthalmology, vol. 116, No. 4, Apr. 2009, pp. 691-701 (11 pages).

Stanley PF, Tanzer DJ, Schallhorn SC, "Laser Refractive Surgery in the United States Navy," Current Opinion Ophthalmology, vol. 19, Jul. 2008, pp. 321-324 (4 pages).

Strenk SA, Strenk LM, Koretz JF, "The Mechanism of Presbyopia," Progress in Retinal Eye Research, vol. 24, May 2005, pp. 379-393 (15 pages).

Stringer H, Parr J., "Shrinkage Temperature of Eye Collagen," Nature, Dec. 1964, p. 1307 (1 page).

Sutton G., Patmore A.L., Joussen A.M., Marshall J., "Mannose 6-Phosphate Reduces Haze Following Excimer Laser Photorefractive Keratectomy," Lasers and Light, vol. 7, No. 2/3, 1996, pp. 117-119 (3 pages).

Telandro A., "Pseudo-Accommodation Cornea: a New Concept for Correction of Presbyopia," *Journal of Refractive Surgery*, vol. 20, No. 5, Sep.-Oct. 2004, pp. S714-S717 (5 pages).

Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).

Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).

Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).

Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).

Wang JQ, Zeng YJ, Li XY, "Influence of Some Operational Variables on the Radial Keratotomy Operation," *British Journal of Opthamology*, vol. 84, Jan. 2000, pp. 651-6533 (4 pages).

Wollensak, G., et al., "Riboflavin/Ultraviolet-A-Induced Collagen Crosslinking for the Treatment of Keratoconus," American Journal of Ophthalmology, *Ophthalmic Publ.*, Chicago, IL, US, vol. 135, No. 5, May 1, 2003, pp. 620-627 (8 pages).

Zelichowska B, Rękas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).

International Search Report for PCT/US2010/029806 dated Jun. 1, 2010 (3 pages).

Written Opinion for PCT/US2010/029806 dated Jun. 1, 2010 (6 pages).

International Search Report for PCT/US2010/029791 dated Jun. 1, 2010 (3 pages).

Written Opinion for PCT/US2010/029791 dated Jun. 1, 2010 (6 pages).

Trembly et al.; Microwave Thermal Keratoplasty for Myopia: Keratoscopic Evaluation in Porcine Eyes; Journal of Refractive Surgery; vol. 17; Nov./Dec. 2001; (8 pages).

PCT International Search Report for International Application No. PCT/US2009/0059260 dated Dec. 8, 2009 (2 pages).

Written Opinion corresponding to International Patent Application Serial No. PCT/ U52009/059260, United States Patent Office; dated Dec. 8, 2009 (14 pages).

Chandonnet, CO2 Laser Annular Thermokeratoplasty: A Preliminary Study, Lasers in Surgery and Medicine 12:264-273 (1992), Wiley-Lill, Inc.

Muller et al., Br. J. Opthalmol 2001; 85:437-443 (April).

Naoumidi et al., J. Cataract Refract Surg. May 2006; 32(5):732-41.

Pallikaris et al., J. Cataract Refract Surg. Aug. 2005; 31(8):1520-29.

Acosta et al., Cornea. Aug. 2006;25(7):830-8.

Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.

Berjano et. al.; "Ring Electrode for Radio-Frequency Heating of the Cornea: Modelling and In Vitro Experiments"; Medical & Biological Engineering & Computing 2003; vol. 41; pp. 630-639.

International Search Report mailed Aug. 14, 2009 for PCT/US2009/042204, (5 pages).

International Search Report mailed Nov. 20, 2009 for PCT/2009/059061 (3 pages).

International Search Report mailed Nov. 6, 2009 for PCT/US2009/057481 (2 pages).

Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).

\* cited by examiner

EYE THERAPY SYSTEM

CROSS REFERENCE TO RELATED APPLICATIONS

This application claims priority to U.S. Provisional Application No. 61/101,820, filed Oct. 1, 2008, the contents of which are incorporated entirely herein by reference.

BACKGROUND OF THE INVENTION

1. Field of the Invention

The invention pertains to the field of keratoplasty and, more particularly, to methods and systems employing an applicator to deliver energy according to a selected pattern to correct eye disorders.

2. Description of Related Art

A variety of eye disorders, such as myopia, astigmatism, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratomileusis (LASIK), may be employed to reshape the cornea. However, such surgical procedures may typically require an extended healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy according to particular patterns may cause aspects of the cornea to flatten and improve vision in the eye.

SUMMARY OF THE INVENTION

Embodiments according to aspects of the present invention provide improved methods and systems for using an applicator to deliver energy to the eye according to selected patterns to correct eye disorders. In particular, embodiments employ a sheath that is removably fitted to an energy applicator.

In one aspect, the sheath provides a dielectric layer that provides an electrical insulator to minimize the concentration of electrical current in the area of contact between the eye surface and the energy applicator. In another aspect, the sheath allows the eye to be cooled during the application of energy without directly applying coolant to the eye.

In a further aspect, the sheath includes a dielectric layer that may be configured to provide varying impedances that provide different patterns for energy delivery to the eye. As such, a single energy applicator may be employed with different sheaths to deliver energy to the eye according to different patterns. In other words, the sheath may be employed to customize a standard energy applicator and eliminate the need for multiple applicators with fixed configurations and/or fixed dimensions. Moreover, the different patterns may include asymmetric, non-annular, and/or irregular shapes to treat disorders such as astigmatism.

In yet another aspect, the sheath may be removed from the applicator and replaced after each use. Thus, the disposable nature of the sheath promotes hygienic use of the applicator, as direct patient contact can be limited to the sheath. Replacing the sheath after each use ensures that there is no cross-contact between patients.

Accordingly, an embodiment according to aspects of the present invention provides an energy conducting system for applying therapy to an eye. The system includes a conducting element. The conducting element is configured to conduct energy from an energy source to apply therapy to an eye. The system also includes a covering configured to be removably attached to the conducting element. The covering has an interface surface that is positionable at an eye. At least a portion of the interface surface includes one or more dielectric materials. The energy from the energy conducting element is deliverable to the eye through the interface surface.

Another embodiment according to aspects of the present invention provides a device for insulating a portion of a conducting element. The conducting element is configured to deliver energy from an energy source to provide therapy to an eye. The device includes a covering that defines an interface surface positionable at an eye. At least a portion of the interface surface includes one or more dielectric materials. Energy from the conducting element is deliverable to the eye through the interface surface. The device also includes an attachment element coupled to the covering. The attachment element is removably attachable to the conducting element and is configured to position the interface surface relative to the conducting element.

Yet another embodiment provides, an energy conducting system for applying therapy to an eye. The system includes a conducting element including a first electrode and a second electrode. The first electrode and the second electrode are separated by a gap. The conducting element is configured to deliver energy from an energy source to a distal end. The system includes a covering disposed at the distal end of the conducting element. The covering defines an interface surface positionable at an eye. The interface surface includes one or more dielectric materials and one or more conductive materials. Energy from the conducting element is deliverable to the eye through the interface surface.

These and other aspects of the present invention will become more apparent from the following detailed description of the preferred embodiments of the present invention when viewed in conjunction with the accompanying drawings.

DESCRIPTION

Figure 1:
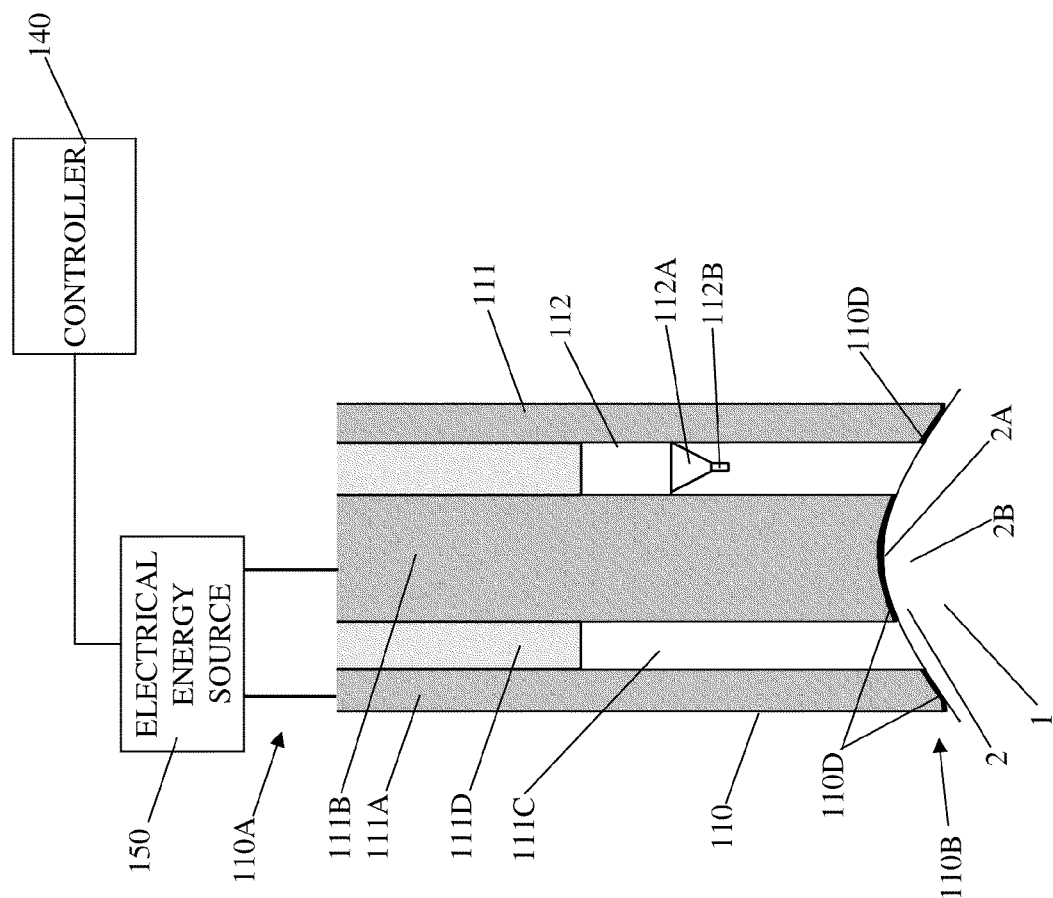
FIG. 1 illustrates an example system for applying energy to a cornea of an eye to cause reshaping of the cornea according to aspects of the present invention.

FIG. 1 illustrates an example system for applying energy to a cornea 2 of an eye 1 to generate heat and cause reshaping of the cornea. In particular, FIG. 1 shows an applicator 110 with an electrical energy conducting element 111 that is operably connected to an electrical energy source 150, for example, via conventional conducting cables. The electrical energy conducting element 111 extends from a proximal end 110A to a distal end 110B of the applicator 110. The electrical energy conducting element 111 conducts electrical energy from the source 150 to the distal end 110B to apply energy to the cornea 2, which is positioned at the distal end 110B. In particular, the electrical energy source 150 may include a microwave oscillator for generating microwave energy. For example, the oscillator may operate at a microwave frequency range of 400 MHz to 3000 MHz, and more specifically at a frequency of around 915 MHz or 2450 MHz. As used herein, the term "microwave" may correspond to a frequency range from about 10 MHz to about 10 GHz.

As further illustrated in FIG. 1, the electrical energy conducting element 111 may include two microwave conductors, or electrodes, 111A and 111B, which extend from the proximal end 110A to the distal end 110B of the applicator 110. In particular, the conductor 111A may be a substantially cylindrical outer conductor, while the conductor 111B may be a substantially cylindrical inner conductor that is disposed in an inner passage extending through the outer conductor 111A. With the inner passage, the conductor 111A may have a substantially tubular shape. The outer conductor 111A and inner conductor 111B may be formed, for example, of aluminum, stainless steel, brass, copper, other metals, coated metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 150, and directs microwave energy to the distal end 110B, where the cornea 2 is positioned.

The outer diameter of the inner conductor 111B is preferably larger than the pupil. In general, the outer diameter of the inner conductor 111B may be selected to achieve an appropriate change in corneal shape, i.e., keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of heat by the applicator 110.

In other systems, the outer conductor 111A and the inner conductor 111B may be dimensioned to have very small diameters, so that the energy conducting element 111 essentially applies energy to the cornea 2 in a point, rather than in an annular shape. In other words, the energy conducting element 111 may provide a pen-like device that shrinks corneal collagen at a selected area of very small diameter. In operation, such systems employ the energy conducting element 111 to shrink corneal collagen at a series of points and the combination of spot treatments results in the desired reshaping of the cornea 2.

A controller 140 may be employed to selectively apply the energy any number of times according to any predetermined or calculated sequence. The controller 140 may include a computer device to control the application of energy according to instructions provided via a computer-readable storage medium. In addition, the controller 140 may include a monitor and keyboard, or other user interface devices for receiving instructions from an operator.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric layer 110D may be employed along the distal end 110B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 51.μm (0.002 inches). In general, an interposing layer, such as the dielectric layer 110D, may be employed between the conductors 111A and 111B and the cornea 2. However, the interposing layer does not substantially interfere with the strength and penetration of the microwave radiation field in the cornea 2. Moreover, the interposing layer does not prevent sufficient penetration of the microwave field and generation of a desired heating pattern in the cornea 2. The dielectric material may be an elastic material, such as polyurethane or silastic. Alternatively, the dielectric material may be a non-elastic material, such as Teflon® or polyimides. The dielectric material may have a fixed dielectric constant or varying dielectric constant by mixing materials or doping the sheet, the variable dielectric being spatially distributed so that it may affect the microwave heating pattern in a customized way. The thermal conductivity of the material may have fixed thermal properties (thermal conductivity or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating. Embodiments employing dielectric layers of varying thickness are described further below.

As FIG. 1 also illustrates, the applicator 110 may also include a micro-controller coolant delivery system 112. The micro-controlled coolant delivery system 112 is in fluid communication with a coolant supply (not shown) and pulses of coolant, or cryogen, from the coolant supply may be applied toward the corneal surface 2A before, during, and/or after energy is applied to the cornea 2 with the electrical energy source 150 and the electrical energy conducting element 111. As such, the applicator 110 may be employed to apply coolant to selectively cool the surface 2A of the cornea 2 positioned at the distal end 110B. The delivery of coolant from the coolant delivery element 112 toward the corneal surface 2A, in sequence with the application of heat to the cornea 2, permits the corneal temperature to be increased to cause appropriate shrinkage of the collagen fibers in the targeted mid-depth region 2B and reshape the cornea 2, while also minimizing injury to the outer layer 2A, i.e. the epithelium, of the cornea 2.

The coolant delivery system 112 may have a nozzle structure 112A with an opening 112B directed toward the distal end 110B. Although FIG. 1 may illustrate one nozzle structure 112A, the coolant delivery system 112 may include more than one nozzle structure 112A arranged, for example, circumferentially within the annular gap 111C. Although FIG. 1 may illustrate the nozzle structure 112A, other embodiments may employ other types of outlets or ports for delivering coolant to the surface 2A or other areas of the eye 1.

Furthermore, the applicator 110 may define a substantially enclosed assembly at the distal end 110B, which is placed in contact with the corneal surface 2A. As shown in FIG. 1, this enclosed assembly may house the energy conducting element 111 and the coolant delivery element 112. In some embodiments, the dielectric layer 110D may provide a membrane-like layer substantially enclosing the distal end 110B of the applicator 110. In this case, the coolant delivery system 112 applies coolant to the dielectric layer 110D, rather than directly to the eye 1.

The controller 140 may also be operably connected to the coolant delivery system 112 as well as the energy source 150. As such, the controller 140 may be employed to determine the amount and timing of coolant delivered from the coolant delivery system 112 toward the corneal surface 2A at the distal end 110B. The controller 140 may be employed to selectively apply the heat and the coolant any number of times according to a predetermined or calculated sequence. For instance, the coolant may be applied to the corneal surface 2A before, during, or after the application of heat to the cornea 2, or any combination thereof.

In some embodiments, the coolant delivery system 112 may employ a solenoid valve in combination with the delivery nozzle 112A. As is known, a solenoid valve is an electromechanical valve for use with liquid or gas controlled by applying or stopping an electrical current through a coil of wire, thus changing the state of the valve. As such, the controller 140 may electronically control the actuation of the solenoid valve to deliver the coolant through the delivery nozzle 112A to the corneal surface 2A. However, other embodiments may employ other types of actuators or alternative techniques for delivering coolant through the delivery nozzle 112A in place of a solenoid valve.

During operation of the embodiment of FIG. 1, the controller 140 may be used to actuate the application of micro-controlled pulses of coolant to the corneal surface 2A before the application of heat to the cornea 2. A pulse, or a spurt, of coolant is applied to the corneal surface 2A for a predetermined short period of time so that the cooling remains generally localized at the corneal surface 2A while the temperature of deeper corneal collagen fibers 2B remains substantially unchanged. Preferably, the pulse is on the order of milliseconds and is less than 100 milliseconds. The delivery of the coolant to the corneal surface is controlled by the controller 140 and may be less than 1 millisecond. Furthermore, the time between the application of the coolant and the application of the heat is also controlled by the controller 140 and may also be less than 1 millisecond. The coolant pulse generally covers an area of the corneal surface 2A that corresponds with the application of heat to the cornea 2. The shape, size and disposition of the cooled region may be varied according to the application.

Advantageously, localized delivery of coolant to the corneal surface 2A before the application of heat to the cornea 2 minimizes the resulting temperature at the corneal surface 2A when the heat is applied, thereby minimizing any heat-induced injury to the corneal surface 2A. In other words, the coolant reduces the temperature of the corneal surface 2A, so that the maximum surface temperature achieved at the corneal surface 2A during or immediately after heat exposure is also reduced by a similar magnitude when compared to a case where no coolant is applied prior to heat exposure. Without the application of coolant, the temperature at the corneal surface 2A rises during or immediately after heat exposure with persistent surface heating resulting from a slow dissipation of heat trapped near the surface-air interface.

Although temperatures observed at the corneal surface 2A immediately after heat exposure are lowered by the application of coolant before exposure, a delayed thermal wave may arrive at the corneal surface 2A after exposure as the heat generated in the corneal areas 2B below the surface 2A diffuses toward the cooled surface 2A. The heat transfer from the corneal surface 2A to the surrounding air is likely to be insignificant, because air is an excellent thermal insulator. With no cooling after the application of heat, heat diffusing away from the areas 2B beneath the corneal surface 2A builds up near the corneal surface 2A and produces an elevated surface temperature that may persist after the application of heat. Although the heat that builds up near the corneal surface 2A may eventually dissipate through thermal diffusion and cooling via blood perfusion, such dissipation may take several seconds. More immediate removal of this heat by additional application of coolant minimizes the chances for heat-related injury to the corneal surface 2A. Thus, embodiments may employ not only a pulse of coolant immediately prior to heat exposure, but also one or more pulses of coolant thereafter. Accordingly, in further operation of the embodiment of FIG. 1, the controller 140 may also be used to apply micro-controlled pulses of coolant during or after the applicator 110 applies heat to the cornea 2, or any combination thereof. This application of coolant rapidly removes heat which diffuses from the mid-depth corneal region 2B to the corneal surface 2A.

When the coolant delivery system 112 delivers the pulse of coolant to the corneal surface 2A, the coolant on the corneal surface 2A draws heat from the surface 2A, causing the coolant to evaporate. In general, coolant applied to the surface 2A creates a heat sink at the surface 2A, resulting in the removal of heat before, during, and after the application of heat to the cornea 2. The heat sink persists for as long as the liquid cryogen remains on the surface 2A. The heat sink can rapidly remove the trapped heat at the surface 2A without cooling the collagen fibers in the region 2B. A factor in drawing heat out of the cornea 2 is the temperature gradient that is established near the surface 2A. The steeper the gradient, the faster a given quantity of heat is withdrawn. Thus, the application of the coolant attempts to produce a large surface temperature drop as quickly as possible.

Because the cooled surface 2A provides a heat sink, the amount and duration of coolant applied to the corneal surface 2A affects the amount of heat that passes into and remains in the region underlying the corneal surface 2A. Thus, controlling the amount and duration of the cooling provides a way to control the depth of corneal heating, promoting sufficient heating of targeted collagen fibers in the mid-depth region 2B while minimizing the application of heat to regions outside the targeted collagen fibers.

In general, dynamic cooling of the corneal surface 2A may be optimized by controlling: (1) the duration of the cooling pulse(s); (2) the duty cycle of multiple pulses; (3) the quantity of coolant deposited on the corneal surface 2A so that the effect of evaporative cooling can be maximized; and (4) timing of dynamic cooling relative to heat application. For example, a single pulse timing may include applying a 80 ms heat pulse and a 40 ms cooling pulse at the beginning, middle, or end of the heating pulse. In another example, multiple cooling pulses may be applied according to a pattern of 10 ms ON and 10 ms OFF, with four of these pulses giving a total of 40 ms of cooling, but timed differently.

For example, the coolant may be the cryogen tetrafluoroethane, $C_2H_2F_4$, which has a boiling point of about −26.5° C. and which is an environmentally compatible, nontoxic, nonflammable freon substitute. In another example, the coolant may be a fluorocarbon refrigerant, e.g., R134. The coolant pulse released from the coolant delivery system 112 may include droplets of the cryogen cooled by evaporation as well as mist formed by adiabatic expansion of vapor.

In general, the coolant may be selected so that it provides one or more of the following: (1) sufficient adhesion to maintain good surface contact with the corneal surface 2A; (2) a high thermal conductivity so the corneal surface 2A may be cooled very rapidly prior to heat application; (3) a low boiling point to establish a large temperature gradient at the surface; (4) a high latent heat of vaporization to sustain evaporative cooling of the corneal surface 2A; and (5) no adverse health or environmental effects. Although the use of tetrafluoroethane may satisfy the criteria above, it is understood that embodiments of the present invention are not limited to a particular cryogen and that other coolants, such as liquid nitrogen, argon, or the like, may be employed to achieve similar results. For instance, in some embodiments, other liquid coolants with a boiling temperature of below approximately body temperature, 37° C., may be employed. Furthermore, the coolant does not have to be a liquid, but in some embodiments, may have a gas form. As such, the pulse of coolant may be a pulse of cooling gas. For example, the coolant may be nitrogen ($N_2$) gas or carbon dioxide ($CO_2$) gas.

As described previously, the controller 140 may be employed to selectively apply the heat and the coolant pulses any number of times according to any predetermined or calculated sequence. In addition, the heat and the pulses of coolant may be applied for any length of time. Furthermore, the magnitude of heat being applied may also be varied. Adjusting such parameters for the application of heat and pulses of coolant determines the extent of changes that are brought about within the cornea 2. Of course, as discussed, embodiments of the present invention attempt to limit the changes in the cornea 2 to an appropriate amount of shrinkage of selected collagen fibers. When employing microwave energy to generate heat in the cornea 2, for example with the applicator 110, the microwave energy may be applied with low power (of the order of 40 W) and in long pulse lengths (of the order of one second). However, other embodiments may apply the microwave energy in short pulses. In particular, it may be advantageous to apply the microwave energy with durations that are shorter than the thermal diffusion time in the cornea. For example, the microwave energy may be applied in pulses having a higher power in the range of 300 W to 3 kW and a pulse duration in the range of about 2 milliseconds to about one second. Thus, when applying the coolant pulses before and after the application of heat as discussed previously: a first pulse of coolant is delivered to reduce the temperature of the corneal surface 2A; a high power pulse of microwave energy is then applied to generate heat within selected areas of collagen fibers in a mid-depth region 2B; and a second pulse of coolant is delivered in sequence to end further heating effect and "set" the corneal changes that are caused by the energy pulse. The application of energy pulses and coolant pulses in this manner advantageously reduces the amount to heat diffusion that occurs and minimizes the unwanted impact of heating and resulting healing processes on other eye structures, such as the corneal endothelium. Moreover, this technique promotes more permanent and stable change of the shape of the cornea 2 produced by the heat. Although the application of high powered energy in short pulses has been described with respect to the delivery of microwave energy, a similar technique may be applied with other types of energy, such as optical energy or electrical energy with radio frequency (RF) wavelengths described further below.

The system of FIG. 1 is provided for illustrative purposes only, and other systems may be employed to apply energy to cause reshaping of the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference.

In operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A, though a thin interposing dielectric layer 110D may be disposed between the conductors 111A and 111B and the corneal surface 2A. Accordingly, direct contact helps ensure that the pattern of microwave heating in the corneal tissue has substantially the same shape and dimension as the gap 111C between the two microwave conductors 111A and 111B.

Prior to positioning of the applicator 110 in contact with the corneal surface 2A, the corneal surface 2A may be scanned to make a topographical map showing the shape and curvature of the surface of the cornea. Then, with the conductors 111A and 111B positioned flush with the corneal surface 2A, the treatment may apply durations of microwave pulses to generate heat and reshape collagen. The treatment may also apply coolant pulses to protect the corneal surface. In one aspect, the treatment attempts to shrink the collagen in the cornea 2 and form a precisely controlled annular lesion in approximately the upper 150 μm of the stroma. The microwave treatment raises the temperature of an annulus, just below the surface of the cornea, to a temperature in the range of approximately 60 to 75° C. Using evaporative surface cooling techniques, the system cools the surface of the cornea during treatment to isolate and protect the epithelium and Bowman's membrane from microwave heating. Thus, the treatment is noninvasive, as there is no cutting or penetration of the eye. In one example application, the applicator 110 predictably flattens the central cornea to achieve mild-to-moderate myopic correction (−0.5 to −3.5 diopters, D) without compromising the biomechanical integrity of the cornea.

Accordingly, embodiments according to aspects of the present invention may apply microwave energy emitted from the applicator 110 in a substantially annular pattern around the pupil to shrink stromal collagen and modify the dioptric power of the cornea, while a cooling system acts on the corneal surface to minimize thermal damage to the epithelium. In particular, electric field lines form a fringing pattern that extends into the corneal stroma to a depth determined by the applied power and applicator geometry. This electric field causes the polar water molecules to align themselves with the field; the rapid reversal of the sinusoidally-varying field causes frictional heating by these molecules as they rotate in place. This effect does not require a conduction current to flow through a point of electrical contact between a conductor and tissue; heating is caused by a displacement current.

Although the applicator 110 of FIG. 1 may apply energy according to substantially annular patterns defined by the outer conductor 111A and inner conductor 111B, other embodiments may apply energy to an eye in asymmetrical and/or irregular patterns. Such applications can correct eye disorders such as astigmatism. For example, as discussed previously, the energy conducting element 111 may provide a pen-like device that shrinks corneal collagen at a selected spot of very small diameter. To cause asymmetric and/or irregular reshaping of the cornea 2, the combination of spots may be applied to define an asymmetric and/or irregular pattern. Further description of systems for reshaping of the cornea according to asymmetric and/or irregular patterns are provided in U.S. patent application Ser. No. 12/113,672, filed May 1, 2008, the contents of which are entirely incorporated herein by reference.

Figure 2A:
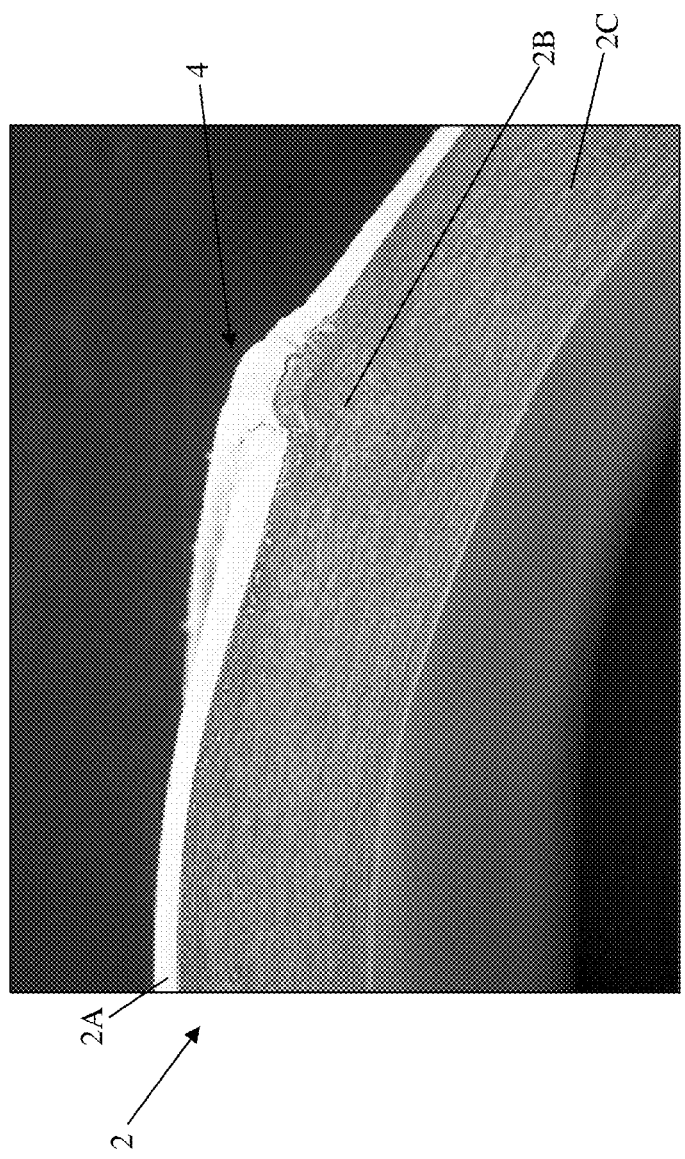
FIG. 2A illustrates a high resolution image of a cornea after heat has been applied.
Figure 2B:
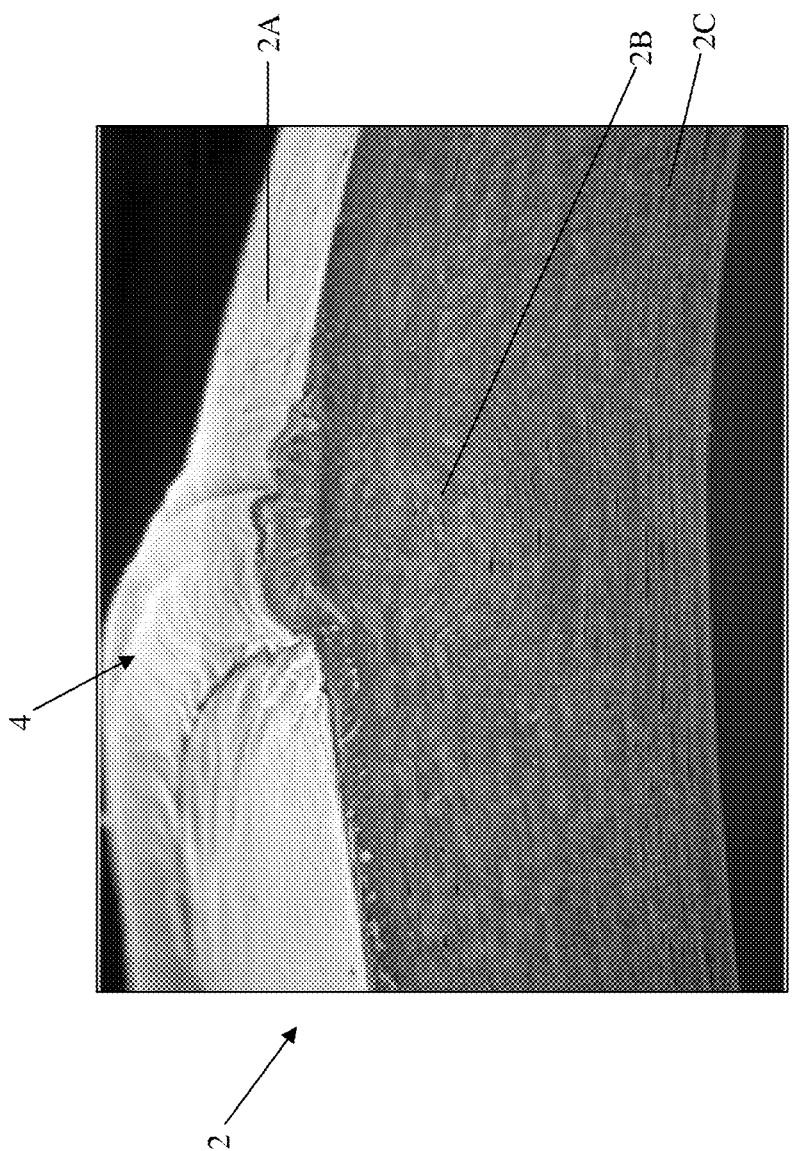
FIG. 2B illustrates another high resolution images image of the cornea of FIG. 2A.

FIGS. 2A-D illustrate an example of the effect of applying heat to corneal tissue with a system for applying heat, such as the system illustrated in FIG. 1. In particular, FIGS. 2A and 2B illustrate high resolution images of cornea 2 after heat has been applied. As FIGS. 2A and 2B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 2C:
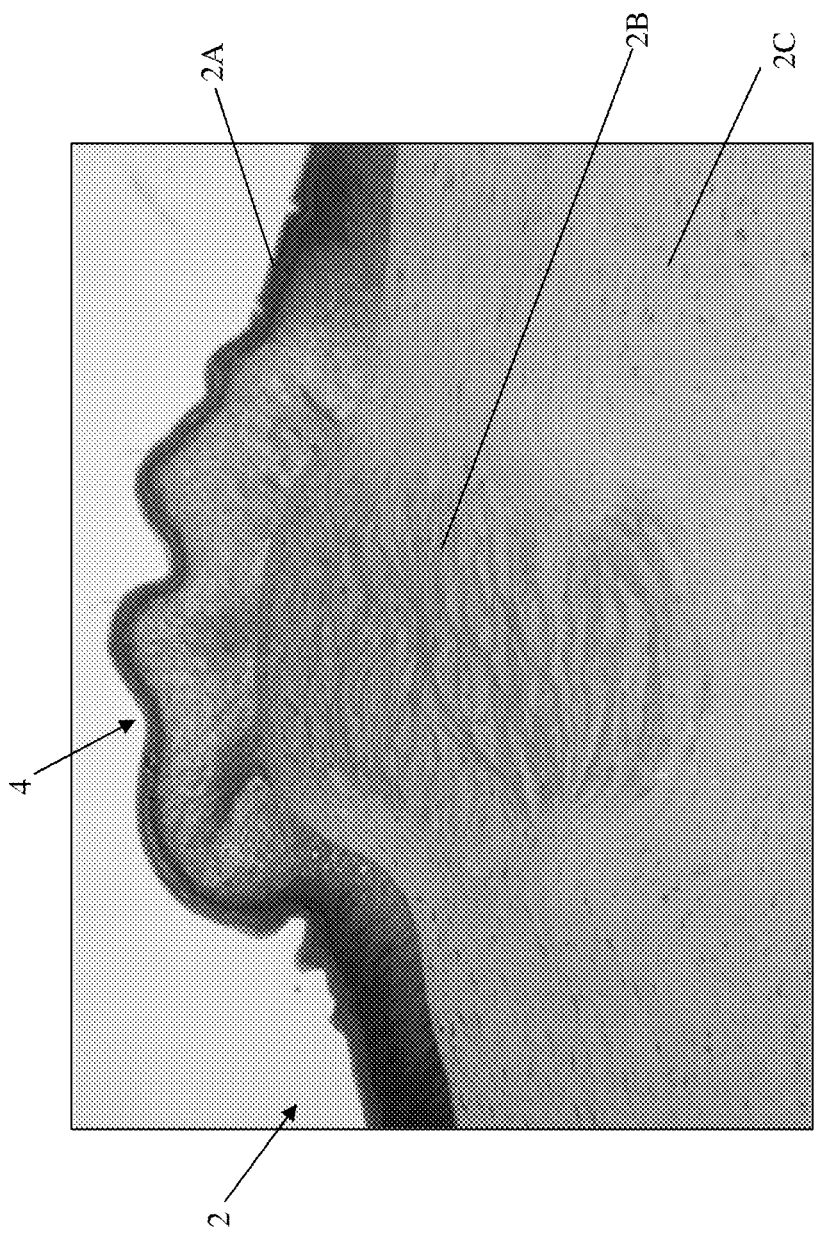
FIG. 2C illustrates a histology image of the cornea of FIG. 2A.
Figure 2D:
FIG. 2D illustrates another histology image of the cornea of FIG. 2A.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, such as orthokeratology, which compress areas of the cornea to reshape the cornea via mechanical deformation, the collagen fibrils in the region 2B are in an entirely new state.

Figure 3:
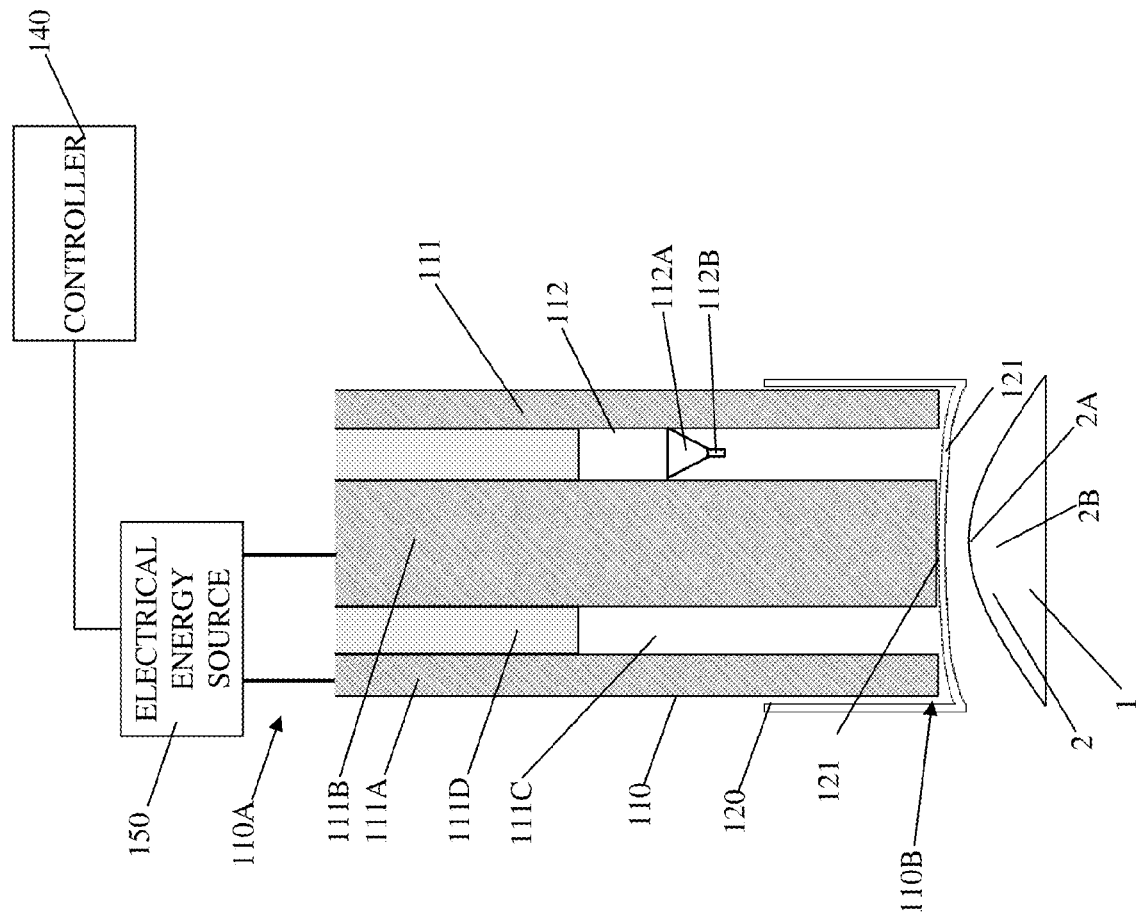
FIG. 3 illustrates an example system that employs a sheath according to aspects of the present invention.

As discussed previously, a dielectric layer 110D may be employed along the distal end 110B of the applicator 110 and positioned between the energy conducting element 111 and the cornea 2. As shown in FIG. 3, the dielectric material does not have to be applied directly to the outer conductor 111A and/or the inner conductor 111B. Rather, a removable sheath, or covering, 120 may be fitted over the distal end 110B of the energy conducting element 111, where the sheath 120 includes a dielectric layer 122 at a contact surface 121. The sheath 120 includes a wall 123, such as, but not limited to, a flexible film material, that defines the contact surface 121. As FIG. 3 illustrates, the contact surface 121 is aligned with the distal end 110B of the applicator 110. When the applicator 110 is applied to the eye 1, the contact surface 121 is disposed between the applicator 110 and the eye 1. As such, the contact surface 121, rather than the applicator 110, comes into direct contact with the eye 1. In other words, the contact surface 121 provides an interface between the patient and the therapy system.

When the sheath 120 is properly fitted, the dielectric layer 122 is disposed in proper relation to the outer conductor 111A and the inner conductor 111B. As described previously, the dielectric layer 122 protects the cornea 2 from electrical conduction current that would otherwise flow into the eye 1 via conductors 111A and 111B. The dielectric layer 122 may be formed from an elastic material, such as polyurethane or silastic. Alternatively, the dielectric layer 122 may be formed from a nonelastic material, such as Teflon® or polyimides. In some embodiments, the entire sheath 120 may be formed from the dielectric material. In other embodiments, the dielectric material is employed only at the contact surface 121 of the sheath 120 to form the dielectric layer 122, while the rest of the sheath 120 is formed from other materials.

As further shown in FIG. 3, the sheath 120 encloses the distal end 110B of the applicator 110. Thus, in operation, the coolant delivery system 112 applies coolant directly to the contact surface 121, rather than directly to the eye. The delivery of coolant sufficiently cools the surface of the cornea during treatment to isolate and protect the epithelium and Bowman's membrane from microwave heating. Advantageously, however, the eye 1 is not directly exposed to the coolant material. In general, the contact surface 121 provides a protective layer over the eye 1 during the operation of the applicator 110.

The sheath 120 may be removed from the applicator 110 and replaced after each use. The disposable nature of the sheath 120 promotes hygienic use of the applicator 110, as the direct contact with the patient's eye can be limited to the contact surface 121. Replacing the sheath 120 after each use helps to ensure that there is no cross-contact between patients.

Figure 4B:
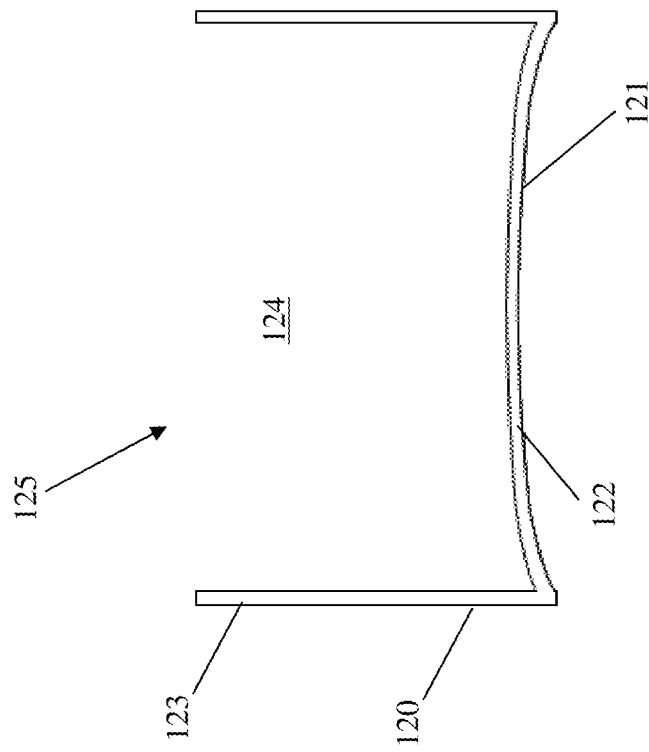
FIG. 4B illustrates a cross-sectional view of the sheath illustrated in FIG. 4A.
Figure 4A:
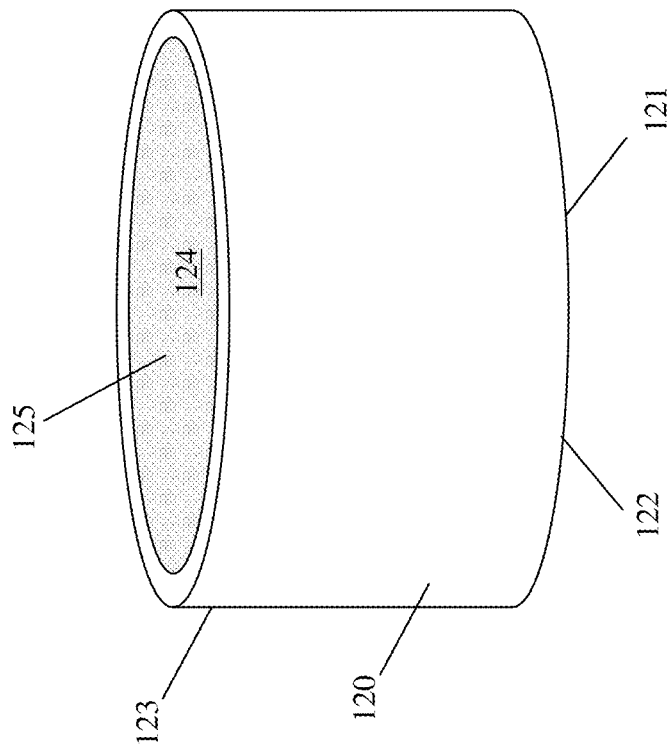
FIG. 4A illustrates an example embodiment of a sheath according to aspects of the present invention.

As shown in FIGS. 4A-B, the sheath 120 may have a substantially cup-like shape that provides a fit over the distal end 110B of the applicator 110. The wall 123 defines a cavity 124. The cavity 124 receives the distal end 110B of the applicator 110 through an opening 125. In some cases, the inner surface of the wall 123 within the cavity 124 may be textured or otherwise treated, e.g., with a non-permanent adhesive, to enhance frictional contact and provide more secure engagement between the sheath 120 and the applicator 110.

FIG. 4B also shows that the contact surface 121 of the sheath 120 may be concave, i.e., curves into the cavity 122. The concave shape of the contact surface 121 minimizes any applanation that the sheath 120 may cause when applied against the eye 1. In other words, the contact surface 121 is not biased outwardly to apply any unwanted additional pressure against the eye 1. Furthermore, the concave shape also promotes more effective contact between the contact surface 121 and the distal end 110B of the applicator 110. Thus, the dielectric layer 122 is properly disposed along the distal end 110B of the applicator 110, and the delivery of energy to the eye 1 is not affected by any gaps or other irregularities between the dielectric layer 122 and the applicator 110.

Figure 5:
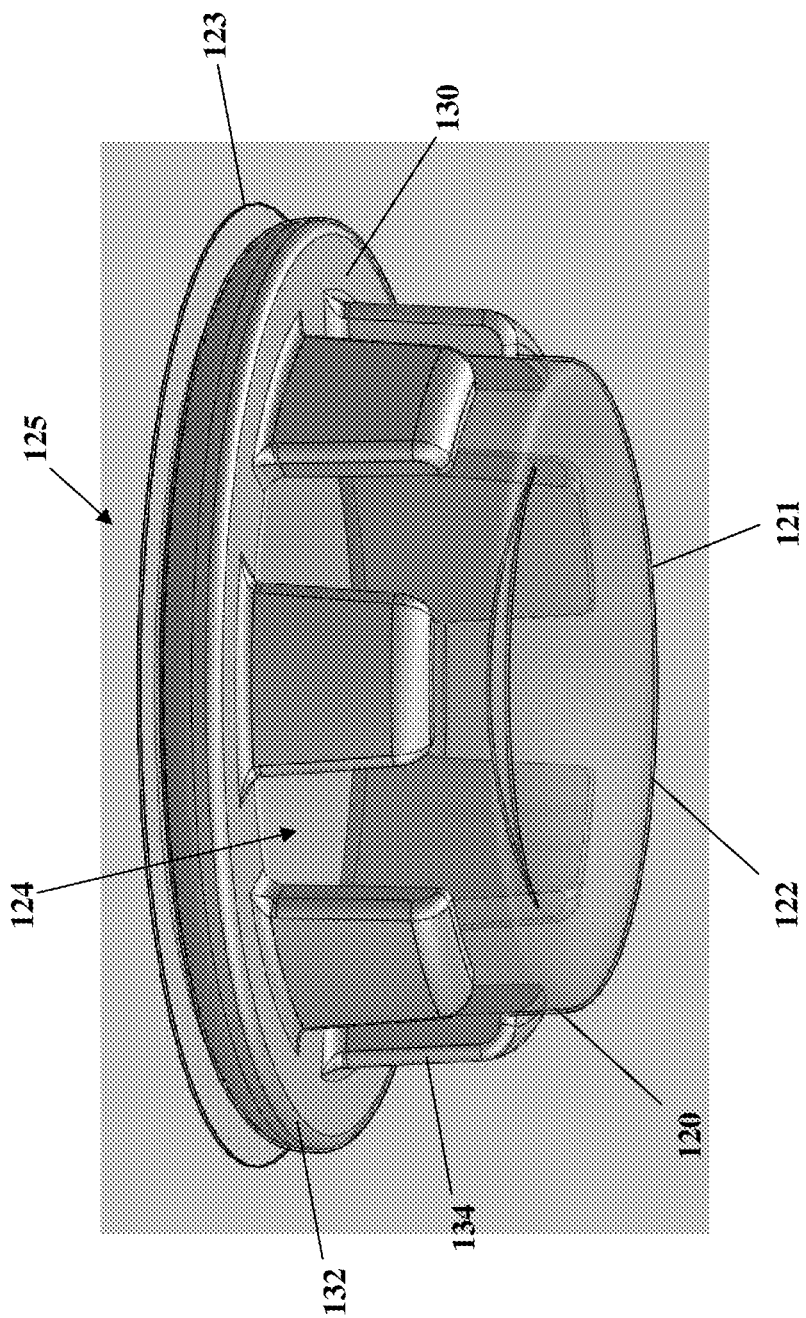
FIG. 5 illustrates another example embodiment of a sheath according to aspects of the present invention.

Aspects of the sheath 120, such as the contact surface 121, may be flexible to fit the contours of the applicator 110. However, more rigid structures may be employed to support the sheath 120. For example, FIG. 5 illustrates a sheath 120 that is supported by a more rigid carrier 130. The carrier 130 facilitates manual handling and positioning of the sheath 120. In one embodiment, the carrier 130 is a molded thermoplastic polyurethane structure, and the sheath 120 is a polyurethane film that is thermally bonded to the carrier 130.

In operation, the carrier 130 engages the periphery of the applicator 110 to provide a tight press-fit and securely position the sheath 120 over the distal end 110B of the applicator 110. The tight press-fit minimizes any relative movement between the sheath 120 and the applicator 110.

As FIG. 5 illustrates further, the carrier 130 includes a collar 132 and a plurality of ribs 134. Together the collar 132 and the ribs 134 provide the substantially cup-like shape for the sheath 120. In particular, the collar 132 maintains the shape, e.g., circular shape, of the opening 125 to the cavity 124. As such, the collar 132 facilitates the insertion of the applicator 110 into the cavity 124. Meanwhile, the ribs 134 are spaced along the circumference of the collar 132 and extend toward the contact surface 121 of the sheath 120. Thus, the ribs 134 support the sides of the sheath 120.

FIG. 5 also shows that the ribs 134 extend radially inward, i.e., angle into the cavity 124, as they extend away from the collar 132. In other words, the diameter across the cavity 124 reduces as the ribs 134 extend away from the collar 132. As a result, when the applicator 110 is inserted farther into the cavity 124, the ribs 134 engage the applicator 110 with greater pressure. This pressure provides a tighter fit between the carrier 130 and the applicator 110. Moreover, the sheath 120 is supported against the applicator 110.

Although FIG. 5 may illustrate a sheath 120 assembled with a separate carrier 130, it is understood that supporting structures may be integral with the sheath 120. For example, structures similar to the collar 132 and the ribs 134 may be formed by increasing the thickness of wall 123 at selected sections of the sheath 120. The thicker sections may provide sufficient rigidity to facilitate handling of the sheath 120 and to fit the sheath 120 securely to the applicator 110. Alternatively, materials of greater rigidity may be incorporated into the walls 123 of the sheath 120. In addition, it is understood that supporting structures for the sheath 120 are not limited to the specific shapes and configurations described herein. Moreover, it is understood that other embodiments may employ other structures or mechanisms that removably fit a desired dielectric layer at the distal end of an applicator.

Figure 4C:
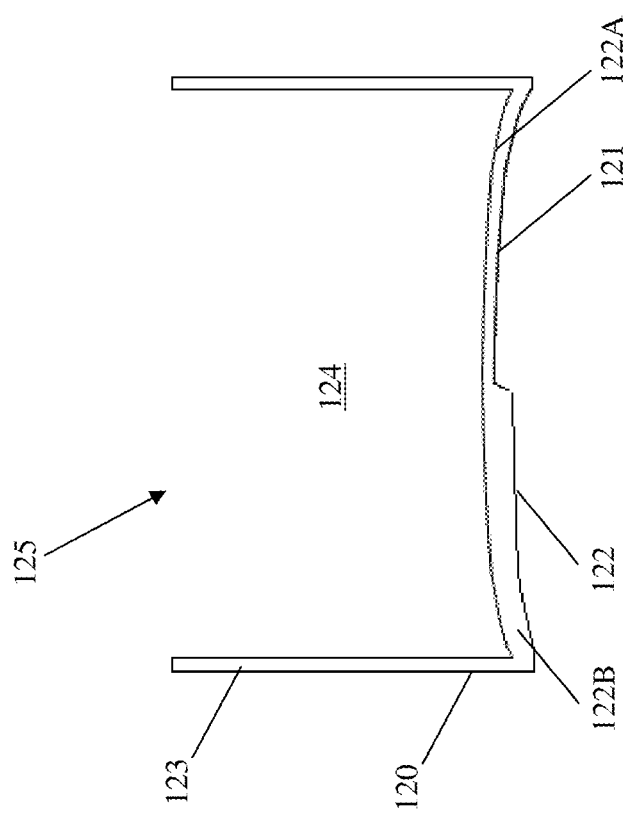
FIG. 4C illustrates a cross-sectional view of a sheath including a dielectric layer of varying thickness according to aspects of the present invention.

As shown in FIG. 5, the sheath 120 may have a substantially uniform thickness. For example, the film may be approximately 50 μm in thickness. However, in other embodiments, the thickness of the sheath 120 may vary. In particular, the dielectric layer 122 along the contact surface 121 may have varying thickness. By way of example, as shown in the cross-sectional view of FIG. 4C, the dielectric layer 122 includes a first section 122A and second section 122B, where the second section 122B is thicker than the section 122A. As discussed previously, varying the thickness of a dielectric layer provides a technique for determining the pattern of energy delivered to the cornea.

The presence of a dielectric layer results in an impedance that affects the delivery of energy through the dielectric layer. A thicker layer of a given dielectric material provides greater impedance. Thus, a dielectric material having sufficient thickness can minimize conductivity. Accordingly, thick sections of dielectric material may be employed along the contact surface 121 to define a selected pattern for delivering energy through the dielectric layer 122. The actual dimensions of the thick sections depend on the material from which the sections are formed. Different materials may require the application of different thicknesses to achieve a given impedance. For example, a polyurethane film of 50 μm does not change the annular pattern defined by the conductors 111A and 111B for the delivery of energy from the applicator 110. However, if sections of the polyurethane film were sufficiently thick, the pattern of energy could be modified from the annular pattern. Alternatively, another material could be employed along the dielectric layer 122 to provide a section of sufficiently high impedance.

Figure 6A:
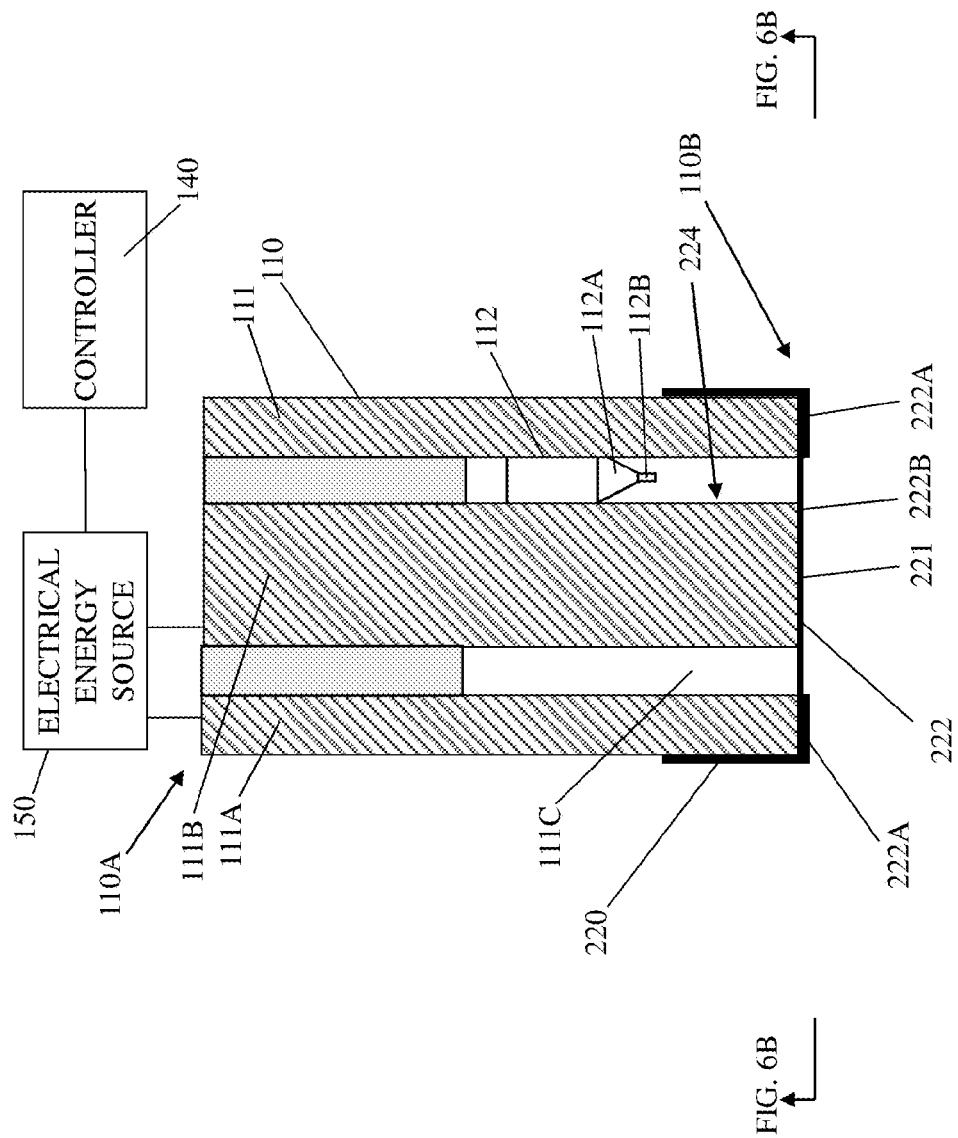
FIG. 6A illustrates an example system that employs a sheath according to aspects of the present invention.
Figure 6B:
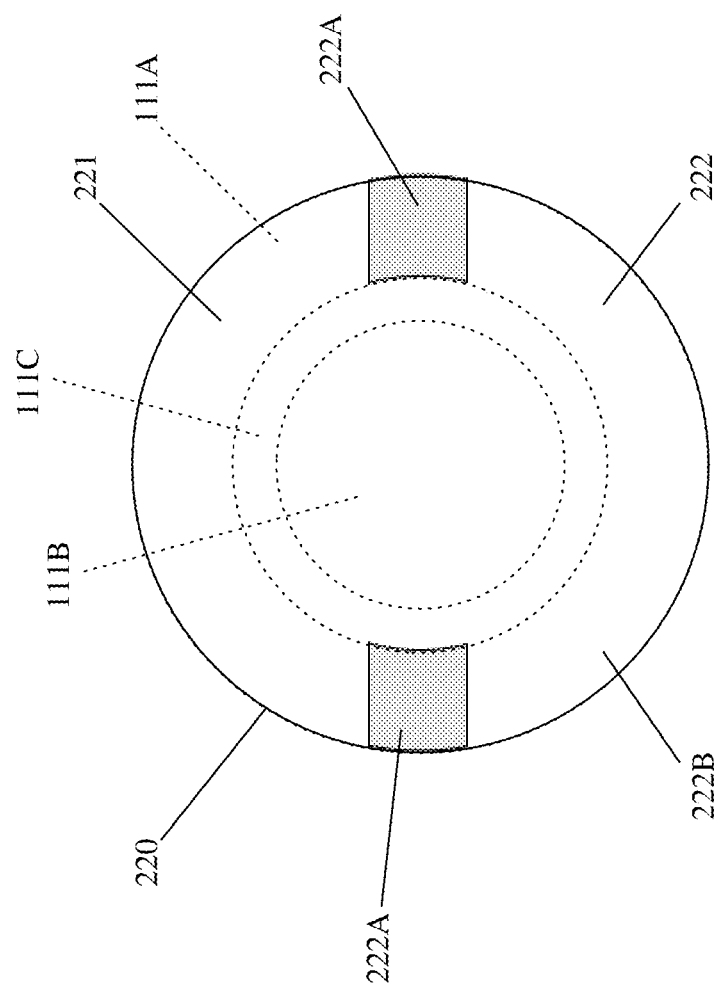
FIG. 6B illustrates the dielectric layer of the sheath illustrated in FIG. 6A.

FIG. 6A illustrates a sheath 220 that may be applied to the applicator 110. The sheath 220 includes a dielectric layer 222 of varying thickness on the contact surface 221. In particular, the dielectric layer 222 includes thick dielectric sections 222A of high impedance and a thin dielectric section 222B of lower impedance. FIG. 6B shows the dielectric layer 222 at the contact surface 221 of the sheath 220. The dotted lines in FIG. 6B identify the outer conductor 111A, the inner conductor 111B, and the gap 111C disposed within the cavity 224. The annular profiles of the outer conductor 111A and the gap 111C are concentric with the circular profile of the inner conductor 111B. FIG. 6B shows that the two thick dielectric sections 222A correspond to opposing sections of the outer conductor 111A. Meanwhile, the thin dielectric section 222B forms the remainder of the dielectric layer 222. Due to the high impedance of the thick dielectric sections 222A, the energy from the energy conducting element 111 is not delivered through the dielectric layer 222 in an annular pattern. In particular, the thick dielectric sections 222A have the effect of segmenting the outer conductor 111A into C-shaped outer conductors, each of which provides a corresponding pattern for energy delivery. The thick dielectric sections 222A effectively prevent the corresponding sections of the outer conductor 111A from forming an electrode pair with the inner conductor 111B and from contributing to the pattern of energy delivered to the eye. Alternatively or additionally, to achieve similar effects, thick sections of the dielectric layer 222 may be aligned with sections of the inner conductor 111B. In this case, these thick sections effectively prevent the corresponding sections of the inner conductor 111B from forming an electrode pair with the outer conductor 111A.

The example of FIGS. 6A-B shows that the thickness of the dielectric layer on a sheath may be varied to change the pattern of energy delivery to the eye. In addition, the example illustrates that the pattern can be non-annular. Furthermore, it can be shown that the dielectric layer can also be configured to produce an asymmetric pattern. For example, in the example of FIGS. 6A-B, an asymmetric pattern can be achieved by implementing only one of the thick dielectric sections 222A. Because the sheath may be employed to deliver energy to the cornea in an irregularly shaped, e.g., asymmetric and/or non-annular, pattern, embodiments according to aspects of the present invention may be employed to treat an eye disorder, such as astigmatism. Furthermore, a sheath that provides a dielectric layer with an asymmetric and/or irregular pattern to treat astigmatism can be more easily reoriented with respect to the applicator or the eye to accommodate the axis of astigmatism. Further examples of asymmetric and/or irregular patterns that can be produced with the sheath described herein are provided in U.S. patent application Ser. No. 12/113,672, filed May 1, 2008, the contents of which are entirely incorporated herein by reference.

Because the sheath can provide a variety of configurations for the dielectric layer, a single energy applicator may be employed with different sheaths to deliver energy to the eye according to different patterns. In other words, the sheath may be employed to customize a standard energy applicator and eliminate the need for multiple applicators with fixed configurations and/or fixed dimensions.

Figure 7:
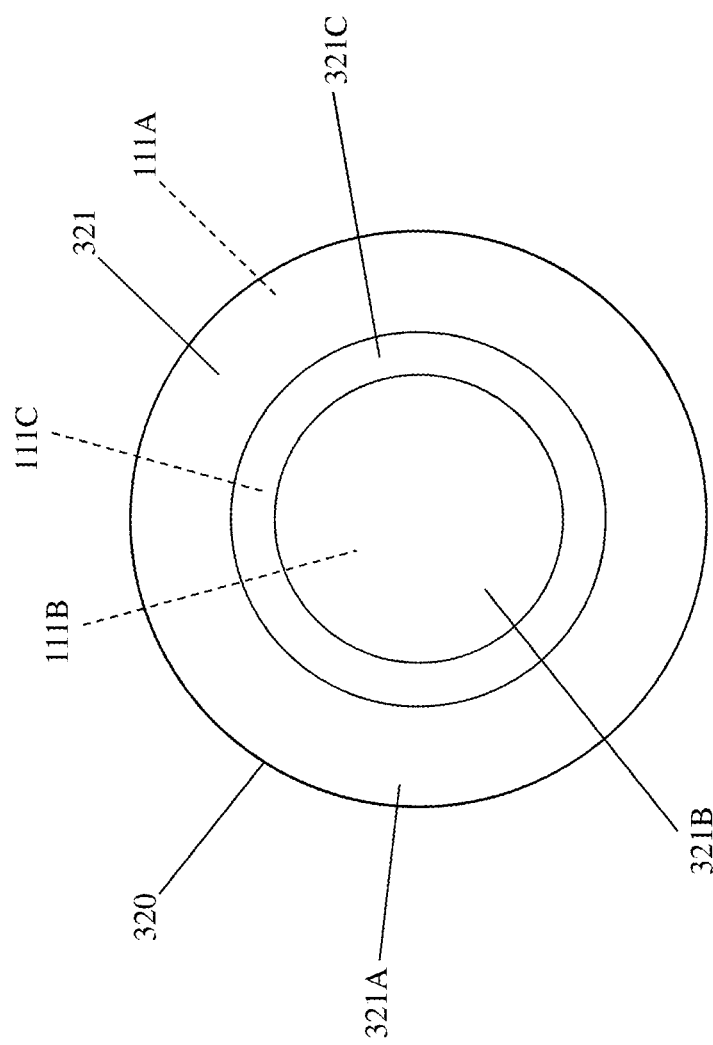
FIG. 7 illustrates a contact surface of another example sheath according to aspects of the present invention.

Embodiments according to aspects of the present invention may employ a variety of materials and/or a variety of thicknesses to configure the contact surface of the sheath. Indeed, as shown in FIG. 7, a contact surface 321 of a sheath 320 does not include an entire layer of one or more dielectric materials. Rather, the contact surface 321 of the sheath 320 includes one or more conductive materials in addition to one or more dielectric materials. For example, the contact surface 321 may include a layer 321A that aligns at least partially with the outer conductor 111A, a layer 321B that aligns at least partially with the inner conductor 111B, and a layer 321C that aligns at least partially with the gap 111C between the conductors 111A and 111B. The layers may be concentric but are not necessarily so. In addition, the layers do not have to coincide completely with features of the energy conducting element. In one embodiment, one or more conductive materials form the layers 321A and 321B, while one or more dielectric materials form the layer 321C. Thus, the contact surface 321 includes two conductive layers separated by a dielectric layer. In another embodiment, one or more conductive materials may form the layer 321A, while one or more dielectric materials form the layers 321B and 321C. Thus, a conductive layer is aligned at least partially with the outer electrode 111A, while a dielectric layer covers the remainder of the contact surface 321. In yet another embodiment, one or more conductive materials may form the layer 321B, while one or more dielectric materials form the layers 321A and 321C. Thus, a conductive layer is aligned at least partially with the outer electrode 111B, while a dielectric layer covers the remainder of the contact surface 321. The use of dielectric materials and conductive materials for the contact surface are not limited to these examples. For example, it is contemplated that any one of the layers 321A, 321B, and 321C may include both conductive and dielectric materials to achieve a particular pattern. It is noted, however, that a conductive path should not extend from the layer 321A and 321B, so that the outer conductor 111A and the inner conductor 111B remain electrically separated. In general, the sheath 320 allows the appropriate lesion to be formed in the corneal tissue, while also providing an intermediate layer that allows coolant to be applied to the eye without direct contact.

While the present invention has been described in connection with a number of exemplary embodiments, and implementations, the present inventions are not so limited, but rather cover various modifications, and equivalent arrangements.

What is claimed is:

1. An energy conducting system for applying therapy to an eye, the system comprising:
   a conducting element, the conducting element being configured to conduct energy from an energy source to a distal end to apply therapy to an eye, the conducting element including a first electrode and a second electrode separated by a gap; and
   a covering configured to be removably attached to the distal end of the conducting element such that at least one of a distal end of the first electrode and a distal end of the second electrode are in direct contact with the covering, the covering having an interface surface positionable at the eye, at least a portion of the interface surface including one or more dielectric materials, the energy from the energy conducting element being deliverable to the eye through the interface surface, the covering being a flexible sheath structure prior to being removably attached to the distal end of the conducting element, the covering being configured to be removed from the distal end of the conducting element as the flexible sheath structure,
   wherein the covering is one of a plurality of removably attachable coverings.

2. The system of claim 1, wherein the covering forms an enclosure over a portion of the conducting element.

3. The system of claim 2, further comprising a coolant delivery system, the coolant delivery system being operable to deliver coolant within the enclosure to cool the interface surface of the covering and the eye, and the enclosure preventing the coolant from directly contacting the eye.

4. The system of claim 1, wherein the covering forms a cavity that receives the conducting element.

5. The system of claim 1, wherein the interface surface is concave.

6. The system of claim 1, wherein the one or more dielectric materials includes polyurethane.

7. The system of claim 1, wherein the energy is delivered through the interface surface according to a pattern defined by the one or more dielectric materials, the one or more dielectric materials providing varying impedances for the interface surface.

8. The system of claim 7, wherein varying impedances are based on the thicknesses of the one or more dielectric materials.

9. The system of claim 7, wherein the interface surface includes sections of high impedance that prevent an electrode pair from forming between corresponding sections of the first electrode and the second electrode.

10. The system of claim 7, wherein the pattern is asymmetric.

11. The system of claim 7, wherein the pattern is non-annular.

12. The system of claim 1, wherein the plurality of removably attachable coverings provide a plurality of patterns for delivering energy through the interface surface.

13. An energy conducting system for applying therapy to an eye, the system comprising:
   a conducting element including a first electrode and a second electrode, the first electrode and the second electrode being separated by a gap, the conducting element being configured to deliver energy from an energy source to a distal end; and
   a covering disposed at the distal end of the conducting element such that at least a portion of the covering extends from the first electrode to the second electrode enclosing the gap at the distal end, the covering being in direct contact with at least one of the first electrode and the second electrode and defining an interface surface positionable at a surface of the eye, the interface surface including one or more dielectric materials and one or more conductive materials, energy from the conducting element being deliverable to the eye through the interface surface, wherein the covering is one of a plurality of removably attachable coverings.

14. The system of claim 13, wherein the interface surface includes at least two conductive layers formed by the one or more conductive materials, the one or more dielectric materials separating the conductive layers.

15. The system of claim 14, wherein the conductive layers include a first conductive layer and a second conductive layer, the first conductive layer being aligned at least partially with the first electrode and the second conductive layer being aligned at least partially with the second electrode, and the one or more dielectric materials separating the first and second conductive layers.

16. The system of claim 13, wherein the interface surface includes one or more conductive layers formed by the one or more conductive materials, the one or more conductive layers being aligned at least partially with at least one of the first electrode and the second electrode.

17. The system of claim 13, wherein the interface surface includes a single conductive layer formed by the one or more conductive materials, the single conductive layer being aligned at least partially with one of the first electrode and the second electrode, the one or more dielectric materials forming the remainder of the interface surface.

18. The system of claim 13, wherein the one or more dielectric materials form a dielectric layer that is aligned at least partially with the gap between the first electrode and the second electrode.

19. The system of claim 13, wherein the first electrode is substantially tubular, the second electrode is substantially cylindrical and disposed in the first electrode, and the gap between the first and second electrode is annular.

20. The system of claim 19, wherein the interface surface includes a single conductive layer formed by the one or more conductive materials, the single conductive layer being aligned at least partially with the first electrode or the second electrode, the one or more dielectric materials forming the remainder of the interface surface.

21. The system of claim 19, wherein the interface surface includes a first conductive layer and a second conductive layer formed by the one or more conductive materials, the first conductive layer being aligned with the first electrode and the second conductive layer being aligned with the second electrode, the one or more dielectric materials forming an annular dielectric layer separating the first and second conductive layers.

22. The system of claim 13, wherein the covering forms an enclosure over the distal end of the conducting element.

23. The system of claim 22, further comprising a coolant delivery system, the coolant delivery system being operable to deliver coolant within the enclosure to cool the interface surface of the covering and the eye, and the enclosure preventing the coolant from directly contacting the eye.

24. The system of claim 13, wherein the covering forms a cavity that receives the conducting element.

25. The system of claim 13, wherein the interface surface is concave.

26. The system of claim 13, wherein the energy is delivered through the interface surface according to a pattern defined by the one or more dielectric materials, the one or more dielectric materials providing varying impedances for the interface surface.

27. The system of claim 26, wherein the varying impedances are based on the thicknesses of the one or more dielectric materials.

28. The system of claim 26, wherein the interface surface includes sections of high impedance that prevent an electrode pair from forming between corresponding sections of the first electrode and the second electrode.

29. The system of claim 26, wherein the pattern is asymmetric.

30. The system of claim 26, wherein the pattern is non-annular.

31. The system of claim 13, wherein the plurality of removably attachable coverings provide a plurality of patterns for delivering energy through the interface surface.

32. An energy conducting system for applying therapy to an eye, the system comprising:
a conducting element including a first electrode and a second electrode, the first electrode and the second electrode being separated by a gap, the conducting element being configured to deliver energy from an energy source to a distal end;
a covering including a contact surface and a wall, the contact surface and the wall defining a cavity, the distal end of the conducting element being disposed within the cavity such that the contact surface is in direct contact with at least one of the first electrode and the second electrode, at least a portion of the contact surface is aligned over the gap at the distal end, the contact surface being positionable at a surface of the eye, the covering including one or more dielectric materials, energy from the conducting element being deliverable to the eye through the contact surface; and
a coolant delivery system, the coolant delivery system being operable to deliver a coolant to the contact surface of the covering, the covering preventing the coolant from directly contacting the eye, the coolant delivery system being positioned to deliver the coolant in the gap between first electrode and the second electrode.

33. The system of claim 32, wherein the covering has a cup shape.

34. The system of claim 32, wherein the contact surface has a concave shape.

35. The system of claim 32, wherein the contact surface has a substantially uniform thickness.

36. The system of claim 32, wherein the wall is disposed along a portion of an exterior surface of the first electrode.

37. The system of claim 32, wherein the first electrode is substantially tubular, the second electrode is substantially cylindrical and disposed in the first electrode, and the gap between the first and second electrode is annular.

38. The system of claim 32, wherein the covering is one of a plurality of removably attachable coverings.

39. The system of claim 38, wherein the plurality of removably attachable coverings provide a plurality of patterns for delivering energy through the interface surface.

40. The system of claim 32, wherein the energy is delivered through the interface surface according to a pattern defined by the one or more dielectric materials, the one or more dielectric materials providing varying impedances for the interface surface.

41. The system of claim 40, wherein varying impedances are based on the thicknesses of the one or more dielectric materials.

42. The system of claim 40, wherein the interface surface includes sections of high impedance that prevent an electrode pair from forming between corresponding sections of the first electrode and the second electrode.

43. The system of claim 40, wherein the pattern is asymmetric.

44. The system of claim 40, wherein the pattern is non-annular.

\* \* \* \* \*